United States Patent

Nuyan

[11] Patent Number: 6,052,194
[45] Date of Patent: Apr. 18, 2000

[54] METHOD AND APPARATUS FOR CONTROLLING THE SPECTRAL REFLECTANCE OF A MATERIAL

[75] Inventor: Seyhan Nuyan, Thornhill, Canada

[73] Assignee: Valmet Automation (Canada) Ltd., Ontario, Canada

[21] Appl. No.: 08/698,493

[22] Filed: Jun. 4, 1996

[51] Int. Cl.⁷ ..................................................... G01J 3/46
[52] U.S. Cl. ........................ 356/402; 356/405; 356/406; 356/408; 356/419; 356/425
[58] Field of Search ..................... 356/402, 405, 356/406, 408, 419, 425

[56] References Cited

U.S. PATENT DOCUMENTS

| | | | |
|---|---|---|---|
| 4,256,131 | 3/1981 | De Remigis | 356/405 X |
| 5,082,529 | 1/1992 | Burk | 356/405 X |
| 5,182,721 | 1/1993 | Kipphan et al. | 364/356 |

*Primary Examiner*—Robert H. Kim
*Attorney, Agent, or Firm*—Shenier & O'Connor

[57] ABSTRACT

A method and apparatus for controlling the color of an article such as a paper web includes performing a comparison between target and measured reflectance values in numerous wavelength bands spanning the visible spectrum. The comparison quantifies correspondingly numerous errors that are modified by a non-linear operation, such as squaring, and then added together. The resulting sum is minimized by individually adjusting the application of a number of colorants to the article. The number of wavelength bands is greater than the number of colorants. This avoids metameric effects which are common in conventional systems that rely on three color space coordinates such as Hunter Laboratories L, a, b; C.I.E. L*, a*, b*; chromaticity x, y, z; and tristimulus X, Y, Z. Colorant response simulators enable the effects of changes in application of colorants to be tested while the actual application of colorants to the article is unchanged.

22 Claims, 6 Drawing Sheets

METHOD AND APPARATUS FOR CONTROLLING THE SPECTRAL REFLECTANCE OF A MATERIAL

BACKGROUND OF THE INVENTION

The instant invention generally relates to governing the amount of a plurality of colorants such as dyes applied to a material to control the reflectance of the material over the entire range of the visible spectrum, and more particularly to controlling the color of a paper web.

In prior art color control systems, the coloration model is generally a 3×3 matrix expressing the relationship between the flows of three judiciously selected colorants and the three color coordinates of one of the common color spaces. These coordinates may be, for example, Hunter Laboratories L, a, b or C.I.E. L*, a*, b* or chromaticity x, y, z or tristimulus X, Y, Z.

Metameric effects are the greatest problem since two differently appearing colors may have the same color coordinates in a given color space. This occurs not only under different illumination and observer conditions, but also simply due to the method in which the various color coordinates are derived.

SUMMARY OF THE INVENTION

One object of my invention is to compare measured reflectance with target reflectance in a plurality of wavelength bands spanning the visible spectrum and adjust the amounts of a plurality of dyes applied to an article accordingly.

Another object of my invention is to provide a color control system wherein the number of wavelength bands at which reflectance values are measured and targeted is greater than the number of dyes.

A further object of my invention is to compare target and measured reflectance values in these wavelength bands while also comparing target and measured color coordinates for a given color space.

A still further object of my invention is to consider the application of a particularly expensive dye as an error that is to be reduced along with other reflectance errors.

Yet another object of my invention is to employ a predictor circuit for paper web coloring that takes into account the time-constant of exponential system response and transport lags or time delays.

A further object of my invention is to provide dye response simulator circuits for paper web coloring which generate the expected change in reflectance over the visible spectrum or in some color space for a change in dye flow so that the effects of a change in dye flow may be evaluated while the actual dye flow is unchanged.

These and other objects of the invention are provided by apparatus for performing a comparison between target and measured reflectance values in a number of wavelength bands spanning the visible spectrum that are greater than the number, nominally at least three, of different dyes the flow rates of which control the measured reflectance values. The comparison quantifies errors that are weighted, nominally by a factor of unity, then modified by a non-linear operation, nominally by squaring or taking the absolute value, and then added together to provide an output that is driven to a minimum by adjusting the individual flow rate of each dye.

Other and further objects of the invention will appear from the following description.

BRIEF DESCRIPTION OF THE DRAWINGS

In the accompanying drawings which form part of the instant specification and which are to be read in conjunction therewith and in which like reference numerals are used to indicate like parts of the various views.

DESCRIPTION OF THE PREFERRED EMBODIMENT

Figure 1:
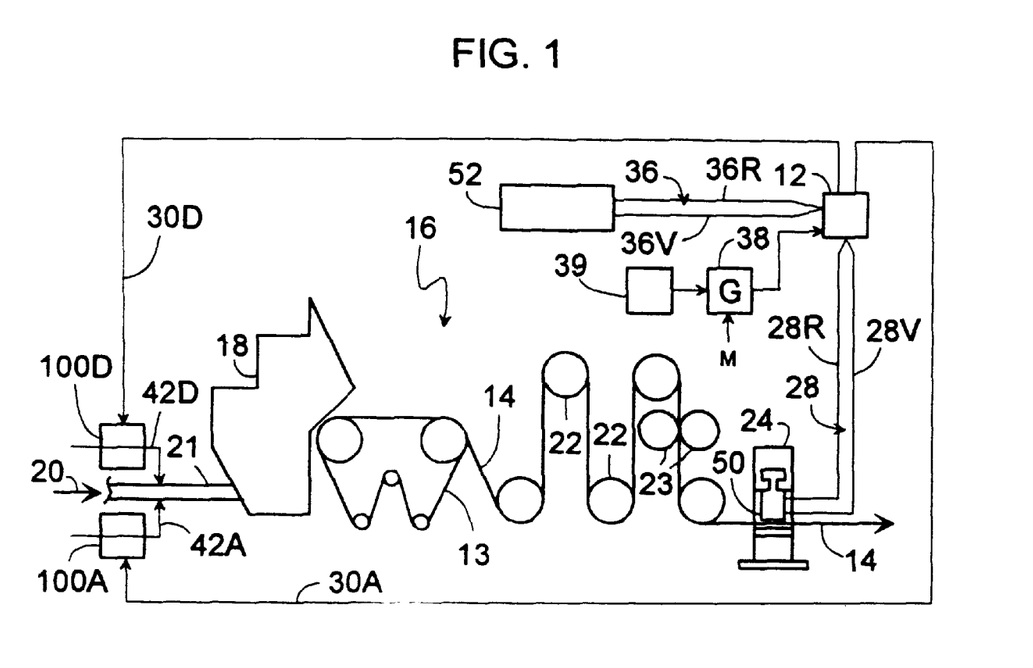
FIG. 1 is a diagrammatic view illustrating the invention and particularly the mechanical deposition of parts.

Referring now to FIG. 1 of the drawings, circuit 12 controls the color of a web of paper 14 produced by a paper mill partially indicated generally by the reference numeral 16. Mill 16 includes a headbox 18 that discharges a wet paper web 14 from a slurry of pulp 20 which flows through pipe 21 to headbox 18. Web 14 is initially supported by a porous belt 13 and acquires strength and form as it passes along rollers 22 to a pair of opposed press rollers 23 which may be used for surface sizing or for pigmented surface coatings. Web 14 eventually passes through a frame 24 along which a spectrophotometer 50 scans the width of paper web 14.

Spectrophotometer 50 senses light reflected from web 14 and passes this information to control circuit 12 in the form of measured reflectance signals indicated generally by the reference numeral 28 taken at a number of wavelength bands, typically thirty or more, spanning the visible spectrum and including a red measurement 28R and a violet measurement 28V. Circuit 12 generates dye flow control signals 30D and additive flow control signals 30A. Also applied to circuit 12 are a target spectrum indicated generally by the reference numeral 36 and comprising wavelength bands corresponding to the measured wavelength bands including a red target reflectance value 36R and a violet target reflectance value 36V. The target spectrum may be the measured reflectance spectrum of a specimen the color of which has been experimentally determined to be desirable. Independently controlled indexers 39 provide signals which are coupled through gates 38 to circuit 12 to change the flow of additives applied to the web 14. A signal M enables gates 38 at certain times as will be described hereinafter.

In response to dye flow control signals 30D from circuit 12, dye flow regulators 100D dispense dyes 42D to control the color of web 14. In response to additive flow control signals 30A, additive regulator 100A dispenses controlled volumes of additives 42A that affect other qualities of paper web 14. The dyes 42D and the additives 42A are all shown injected into pipe 21 at the same distance from headbox 18 to simplify the construction of the predictor circuits to be described subsequently.

Although additives 42A can affect the color of web 14, their primary purpose is to control the quality of the web. A few examples of additives 42A include $TiO_2$ (titanium dioxide) for increasing opacity, $CaCO_3$ (calcium carbonate) for filling voids to provide a smooth surface, sodium aluminum silicate to provide water imperviousness and resistance to heat, rosin or other chemicals for internal sizing to reduce the rate of water penetration, and various retention aids. Such retention aids may include polyacrylamides, polyamine, starch, bentonite clay, alum species, polyethyleneimine, polyethylemeoxide, silica, and polydadamac. These aids are used to increase cleanliness and runability of paper machines, increase production through drainage increases, increase flexibility of fiber furnish substitution, increase efficiency of filler and chemical application, and to reduce fiber loss and close white water systems.

Figure 2:
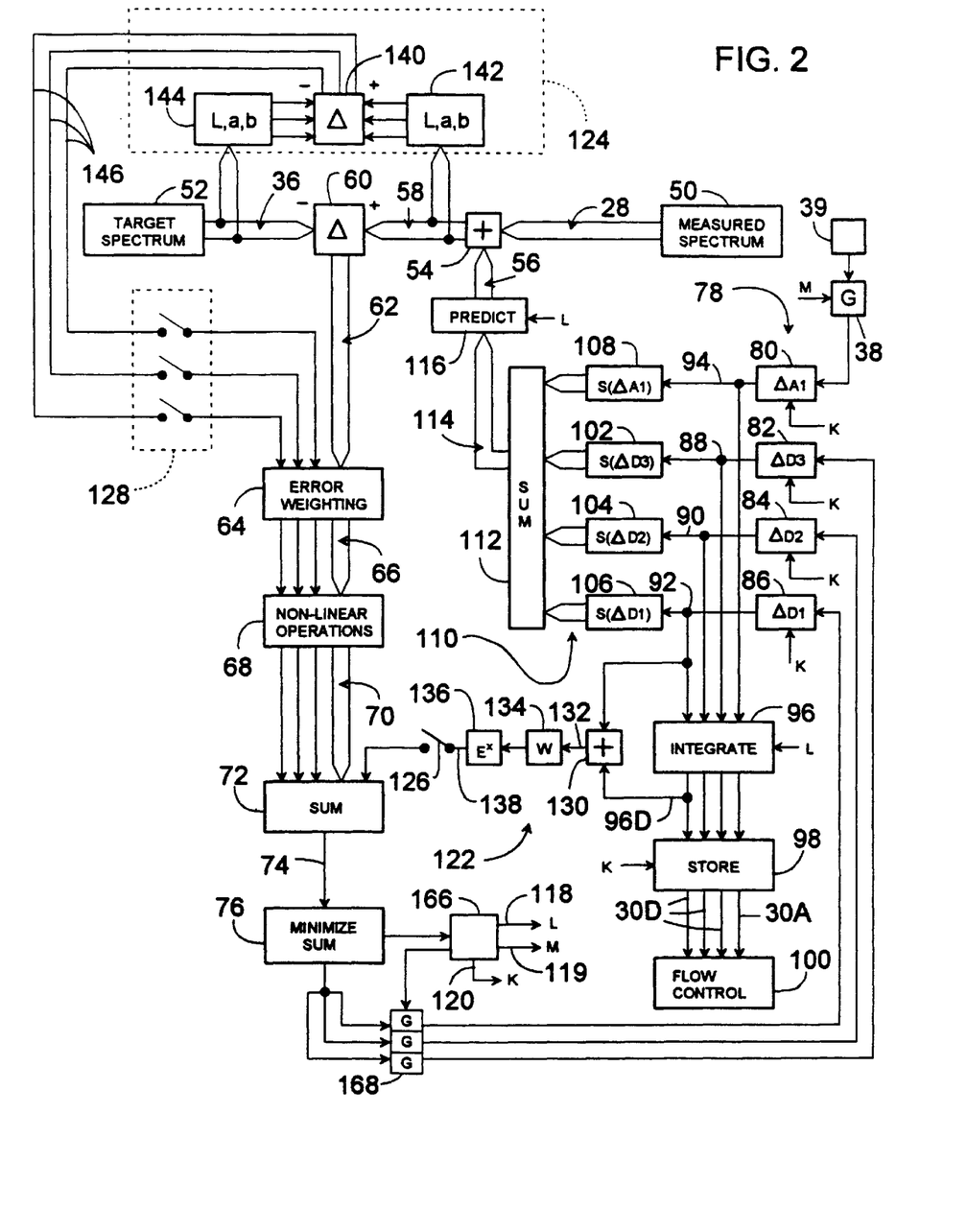
FIG. 2 is a schematic view showing an embodiment of my invention.

FIG. 2 shows a simplified version of circuit 12 which has one additive and modulates the flow rate of three dyes. Measured spectrum 50 may comprise thirty bands of reflectance signals 28 taken in 10 nanometer wavelength bands from 400 to 700 nm. The value of the violet reflectance signal 28V for the band extending from 400 to 410 nm represents the actual reflectance divided by a pure white reference reflectance. The red reflectance signal 28R is measured in the band extending from 690 to 700 nm.

Similarly, target spectrum 52 provides a corresponding thirty desired reflectance signals 36 in 10 nm bands from 400 to 700 nm.

The target spectrum 52 may also be obtained by adjusting the dye flows until measured and target color coordinates in a given color space match one another. The resulting measured spectrum is taken as the target spectrum. This target spectrum may not be unique for the target color coordinates selected; but the system will always provide a measured spectrum closely corresponding to the same metamer.

Circuit 54 adds the values of thirty predicted changes in reflectance signals 56 from circuits 116 to the measured reflectance signals 28 to produce thirty anticipated reflectance signals 58. The anticipated reflectance signals 58 and the target reflectance signals 36 are applied to comparators 60, which subtract target reflectance signals 36 from anticipated reflectance signals 58 to produce thirty error signals 62. A weighting circuit 64 may multiply each error signal by a constant to emphasize or diminish certain regions of the spectrum. Central wavelengths may be diminished or emphasized, low wavelengths may be diminished or emphasized, and high wavelengths may be emphasized or diminished. There results thirty individual weighted error signals 66. The error signals 66 range from positive to negative values and are applied to non-linear operations circuits 68.

Figure 3:
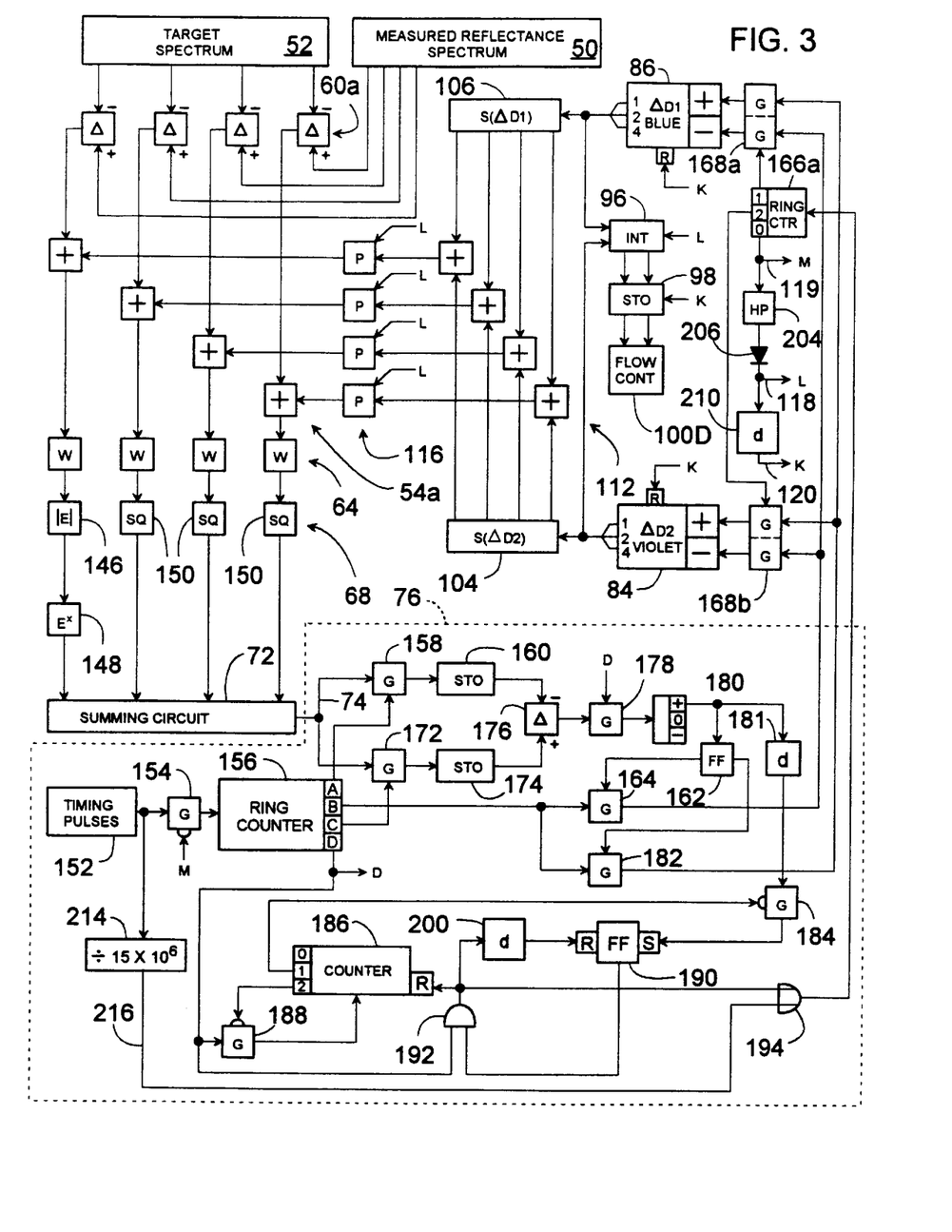
FIG. 3 is a schematic view showing a simplified form of the invention including means for optimizing the flow of two dyes.

Circuits 68 nominally raise each error signal to an even power, such as two, and hence provide a positive output whether the error signal is positive or negative. As shown in FIG. 3, circuit 68 may take the absolute value of an error signal 66 and then raise such absolute value to a power ranging from less than one to more than two.

Non-linear operations circuits 68 provide modified error signals 70 which are applied to a summing circuit 72. Circuit 72 adds together all the modified error signals 70 to produce a sum output 74.

Output 74 is coupled to a sum minimizing circuit 76. In curve fitting approximations the usual criterion is that the sum of the squares of the errors be minimum. Circuit 76 produces changes in the amount of each dye to be applied to the article, web 14, such that output 74 of summing circuit 72 is a minimum. Minimizing circuit 76 performs this function by providing signals which are selectively coupled through sequentially operated gates 168 to index dye counters 82, 84 and 86 up or down in response to changes in value of sum error signal 74. The outputs 88, 90 and 92 of dye counters 82, 84 and 86 represent changes in the flows of respective dyes D1, D2 and D3. Minimizing circuit 76 drives a sequencing circuit 166 providing an output which enables gates 168 to sequentially couple indexing signals from circuit 76 to the dye counters.

Counter circuits 78 include an additive counter 80 as well as the three dye counters. The output 94 of additive counter 80 represents a change in the flow of an additive. Additive counter 80 is indexed by circuit 39 when signal M enables gate 38. Circuit 39 may comprise two manually operable push button switches connected to a positive potential source 255 (FIG. 7) for selectively increasing or decreasing the output of counter 80 one count at a time.

Dye counter outputs 88, 90 and 92 as well as additive counter output 94 from counter circuits 78 are applied to integrating circuits 96, the outputs of which are coupled to storing circuits 98 which provide dye and additive flow control signals 30D and 30A. These in turn are coupled to flow controls 100. Flow controls 100, incorporating flow regulators, such as 100D and 100A of FIG. 1, control the color and other qualities of web 14 by regulating the flow of each dye and additive.

Outputs 88, 90, 92 and 94 from counter circuits 78 are also applied to respective dye response simulator circuits 102, 104 and 106 and to additive response simulator circuit 108. Dye response circuits 102, 104 and 106 each generate the expected change in reflectance over the visible spectrum for a change in dye flow. Similarly, additive response circuit 108 generates the expected change in reflectance over the visible spectrum for a change in additive flow. Response simulator circuits 102, 104, 106 and 108 provide the expected changes in reflectance of web 14 before an actual change is made in the flow of dyes or additives.

The outputs of the dye and additive response circuits, indicated generally by the reference numeral 110, are applied to summing circuits 112. The outputs 114 of summing circuit 112 are the expected changes in reflectance of web 14 over the visible spectrum for the changes in flows of dyes and additives represented by the outputs of counters 78.

Output 114 is applied to a prediction circuit 116 which compensates for the time-constant of exponential change in amount of dye or additive appearing at the output of headbox 18 resulting from a change in flow of dye or additive injected into pipe 21. Prediction circuit 116 also compensates for the time delay or transport lag between the output of headbox 18 and spectrophotometer 50. The thirty outputs 56 of prediction circuit 116 are applied to adding circuit 54 to which is also applied the outputs 28 of spectrophotometer 50 as previously described.

Sequencing circuit 166 generates a signal M on conductor 119, a signal L on conductor 118 and a signal K on conductor 120. Signal L indicates that the sum error 74 has been minimized and activates integrating circuit 96 and prediction circuit 116. Signal K occurs a short time later and resets counter circuits 78 to zero. This ensures that the outputs of the counter circuits 78 are integrated before the counters are reset. Signal M enables gate 38 to couple indexing signals from circuit 39 to additive counter 80.

The embodiment of FIG. 2 includes a circuit indicated generally by the reference numeral 122 for reducing the flow of dye D1 and further includes a color coordinate circuit indicated generally by the reference numeral 124 which circuits are optionally incorporated into control circuit 12 by respective switches 126 and 128. Circuit 122 is useful in reducing the flow of a relatively expensive dye such as D1 by treating any flow of such dye as an error. With switch 126 closed, the flow rate 96D of dye D1 from integrator 96 and the incremental change in flow rate 92 of dye D1 from control counter 86 are added in circuit 130. The output 132 of adding circuit 130 is always positive and is applied to a weighting circuit 134, the output of which is applied to circuit 136, which may raise such output to a power ranging from less than one to more than two. If the power is unity, there is no non-linear operation; and such would not be needed, since the flow of a dye such as D1 can never be negative. The error signal output 138 of circuit 136 is coupled through switch 126 to summing circuit 72.

Turning now to color coordinate circuit 124, the desired or target reflectance signals 36 and the anticipated reflectance signals 58 are applied to respective circuits 144 and 142 for providing color coordinates. As previously indicated, the coordinates may be Hunter Laboratories L, a, b or C.I.E. L*, a*, b* or chromaticity x, y, z for example. The outputs of circuits 144 and 142 are applied to comparator 140, the three error outputs 146 of which are coupled through ganged switches 128 to three corresponding ones of weighting circuits 64. The three corresponding outputs of circuits 64 are applied to three corresponding ones of non-linear operations circuits 68. The three corresponding outputs of circuits 68 are applied to summing circuit 72.

It will be understood that I may similarly provide desired and anticipated color coordinates for a plurality of other color spaces, compare them to provide errors, weight the errors, subject the weighed errors to non-linear operations and apply the modified errors to summing circuit 72.

Optical brightening agents, also known as fluorescent whitening agents, are dyes which absorb, not in the visible spectrum, but in the ultraviolet region and fluoresce or emit in the violet and blue regions. For the purposes of this invention they may be treated either as "dyes" or as additives. It will be understood the "reflectance" spectrum measured by spectrophotometer 50 will include emission in the shorter wavelengths of the visible spectrum where such fluorescent dyes are used.

Figure 10:
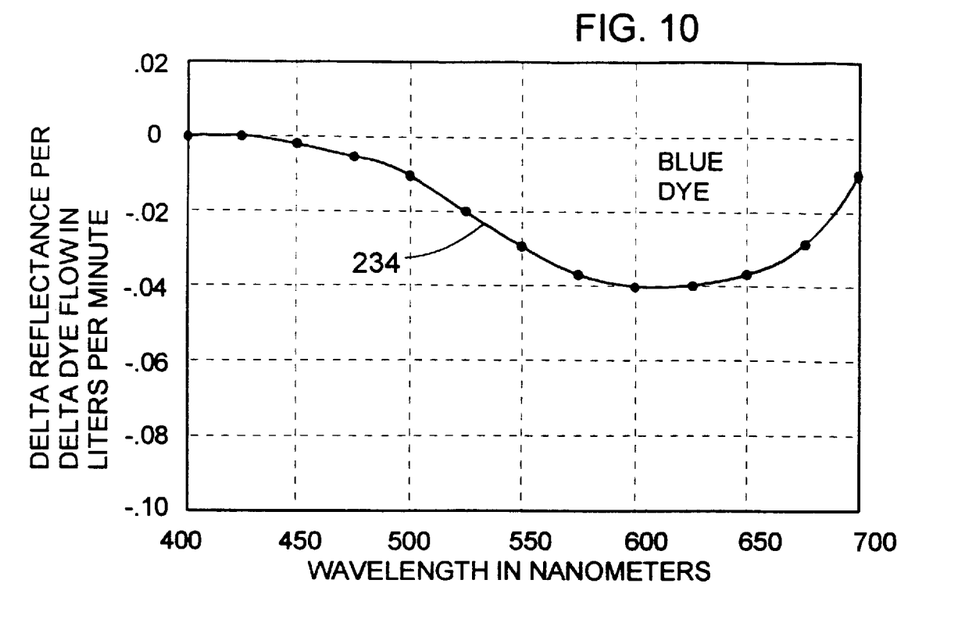
FIG. 10 is a graph of change in reflectance per change in dye flow for a blue dye at thirteen end points of twelve bands in the visible spectrum.

Referring now to FIG. 3, there is shown a simplified circuit for optimizing the flow of two dyes. The number of values of the target and measured spectra has been reduced to four bands extending from 400 nm to 475 nm, from 475 nm to 550 nm, from 550 nm to 625 nm, and from 625 nm to 700 nm, as may be seen from FIG. 11 which shows the normalized spectral response curve 236 of a violet dye D2. FIG. 10 shows the normalized spectral response curve 234 of a blue dye D1 in twelve 25 nm bands covering the visible spectrum, a first band extending from 400 to 425 nm and the twelfth band extending from 675 to 700 nm. The system controls two independent variables, the flow of two dyes, in response to four dependent variables, the measured reflectance signals from four bands of wavelength covering the visible spectrum.

In FIG. 3, comparators 60a provide the differences between target spectrum 52 and measured reflectance spectrum 50; and the outputs of comparator 60a are coupled to summing circuits 54a. The changes in spectra from changes in flow of a blue dye D1 are provided by circuit 106; and the changes in spectra from changes in flow of a violet dye D2 are provided by circuit 104. The outputs of circuits 104 and 106 are summed in adding circuits 112, the outputs of which are applied to prediction circuits 116. The outputs of prediction circuits 116 are coupled to summing circuits 54a. The outputs of summing circuits 54a are applied to corresponding weighting circuits 64, which may be omitted if the weighting of each error signal is unity. The outputs of three of weighting circuits 64 are coupled to corresponding squaring circuits 150. It will be understood that raising an error to an even power yields a positive result whether the error is positive or negative. If the error is raised to other than an even power, then the absolute value of the error signal should first be obtained. The output of the fourth weighting circuit 64 is applied to an absolute value circuit 146, the output of which is applied to a circuit 148 which raises the absolute value of the weighted error signal to a power ranging from less than one to more than two. It will be understood that circuit 148 of FIG. 3 and circuit 136 of FIG. 2 may be omitted if the power to which an error signal is raised is equal to unity. The outputs from the non-linear operation circuits 68 are applied to summing circuit 72.

In FIG. 3, it will be noted that the target and measured reflectance signals are directly compared; and then the predicted changes in reflectance signals are added. The error signals from adding circuits 54a of FIG. 3 will be the same as the error signals from the output of comparator 60 of FIG. 2. The target, measured and predicted signals may be combined either as in FIG. 2 or as in FIG. 3 where no color coordinate error signals are desired. Where color coordinate error signals are desired, then the target, measured and predicted signals should be combined as shown in FIG. 2.

An optimum spectral match occurs when the output 74 of summing circuit 72 is minimized. Timing pulses at a rate, for example, of 1 MHz from source 152 are coupled through gate 154 to a four-stage ring counter 156. Spectrophotometer 50 provides some integration or smoothing of reflectance signals over a time period of ½ second, for example, corresponding to five inches of web width at a scanning speed of ten inches per second. A first pulse "A" from counter 156 actuates gate 158 to store error signal 74 in circuit 160. Assuming that counting flip-flop 162 enables gate 164, the next pulse "B" from counter 156 passes through gate 164. Assuming that sequencing ring counter 166a provides a "1" output enabling gates 168a, the output from gate 164 passes through gates 168a to index a blue dye counter 86 negatively from 0 to −1. The outputs of dye response simulator 106 change from zero in amounts proportional to the normalized dye response curve of FIG. 11. This changes the outputs from adding circuits 112 and ultimately results in a new output 74 from summing circuit 72. The next pulse "C" from counter 156 enables gate 172 to pass this output to storage circuit 174.

If the output of storage circuit 174 is greater than that of circuit 160, the output of comparator 176 will be positive; and on pulse "D" from counter 156, gate 178 will pass this positive output to a polarity discriminator 180, the positive output of which triggers counting flip-flop 162, disabling gate 164 and enabling gate 182. Upon the next "A" pulse from counter 156, the sum error signal 74 will pass through gate 158 and be stored in circuit 160. The next "B" pulse now passes through gate 182 to index counter 170 positively from −1 back to 0 again. The next "C" pulse from counter 156 causes the reduced sum error 74 to be stored in circuit 174. The output of comparator 176 is now negative. Pulse "D" from counter 156 enables gate 178; but discriminator 180 provides no output so that there is no effect on counting flip-flop 162. Successive incrementing of blue dye counter 86 occurs from "B" pulses of ring counter 156 until the error stored in circuit 174 exceeds that in circuit 160, thus providing a positive output from comparator 176. This indicates that, for example, a +4 output from blue counter 86 is one step too great.

The next "D" pulse enables gate 178; and the positive output of comparator 176 passes through gate 178 to discriminator 180 which triggers counting flip-flop 162 and after a delay of 0.1 μsec provided by circuit 181 is applied to gate 184. The first two "D" pulses from counter 156 index a counter 186 through gate 188. A "1" output from counter 186 inhibits gate 184, whereas for a "2" output from counter 186 gate 184 is enabled. The "2" output from counter 186 disables gate 188 so that the count remains "2". The positive output from discriminator 180 now passes through gate 184 to set flip-flop 190. The next "B" pulse from counter 156 now passes through gate 164 to decrement blue dye counter 170 by one step from +4 to +3. The change in the flow rate of the blue dye D1 has now been optimized.

The setting of flip-flop 190 partially enables AND circuit 192. The next "D" pulse from counter 156 enables AND circuit 192. The output of AND circuit 192 is coupled through OR circuit 194 to index sequencing ring counter 166a from "1" to "2". This disables gates 168a and enables gates 168b so that the flow of the violet dye D2 may now be optimized. The optimization of a given dye requires a plurality of "B" inputs from counter 156 to counters 86 and 84. If a count of +1 for counter 86 happens to be optimum, the count will proceed either 0, +1, +2, +1 or 0, -1, 0, +1, +2, +1. If a count of 0 for counter 86 happens to be optimum, the count will proceed either 0, +1, 0, -1, 0, or 0, -1, 0, +1, 0.

It will be noted that on the first "D" pulse from counter 156 a positive output from discriminator 180 will not set flip-flop 190 since a +1 output of counter 186 disables gate 184. It may be further noted that each output from AND circuit 192 resets counter 186 to "0" and, after a 0.1 μsec delay provided by circuit 200, resets flip-flop 190. After violet dye counter 84 has been optimized, the output from AND circuit 192 is coupled through OR circuit 194 to index sequencing ring counter 166a from "2" to "0".

The "0" output of counter 166a provides the M signal 119 which enables gate 38 of FIG. 2 to couple indexing signals from circuit 39 to the additive dye counter 80. During a correction cycle when dye flow counters 84 and 86 are being indexed, there is no M signal; and the output of additive counter 80 cannot be changed. Signal 119 is coupled through a high-pass filter or differentiating circuit 204 and then forwardly through rectifier 206 to provide the L signal 118 which actuates integrators 96 and predictor circuits 116 as shown in FIGS. 2 and 3. The L signal is applied through a 0.1 μsec delay circuit 210 to provide the K signal 120 which actuates storage circuits 98 and resets the dye counters 84 and 86 to zero. The purpose of delay circuit 210 is to permit circuits 96 to complete integration of the changes in dye flow before the incremental dye flow counters 84 and 86 are reset to zero. Again, the outputs of integrators 96 are coupled to storage circuits 98, the outputs of which are applied to the dye flow controllers 100D.

I have assumed that the time-constant of the exponential change in dye flow at the output of the headbox 18 due to changes in dye flow in pipe 21 at the input of the headbox, is 15 seconds. I have further assumed that the time delay or transport lag between the output of headbox 18 and spectrophotometer 50 is 30 seconds. This, for example, might correspond to a speed of web 14 of 2,000 feet per minute and a length of web 14 between headbox 18 and the spectrophotometer 50 of 1,000 feet. The timing pulses are applied to circuit 214 which divides by approximately $15 \times 10^6$ and provides an output once each fifteen seconds. The output 216 of pulse dividing circuit 214 is coupled through OR circuit 194 to index the sequencing ring counter from "0" to "1", thus initiating another correction cycle.

It will be recalled that four cycles of ring counter 156 are required to assure that a 0 output from the blue dye counter 86 is still correct and four more cycles of ring counter 156 are required to assure that a 0 output from the violet dye counter 84 is still correct. The eight cycles of ring counter 156 require 32 timing pulses from source 152. To ensure that measurements will be made and corrections provided to the dye flow controls 100D once each 15 seconds, circuit 214 may divide by only 14,999,968. Once the correction cycle is completed, the M signal 119 from sequencing counter 166a disables gate 154 so that timing pulses from source 152 are no longer applied to ring counter 156.

It will be understood that instead of the sum may be governed by apparatus embodying other methods such as minimizing circuit 76 shown in FIG. 3, the changes in dye flow Newton-Raphson, Davidon-Fletcher-Powell, and Broyden-Fletcher-Goldfarb-Shanno, for example.

Figure 4:
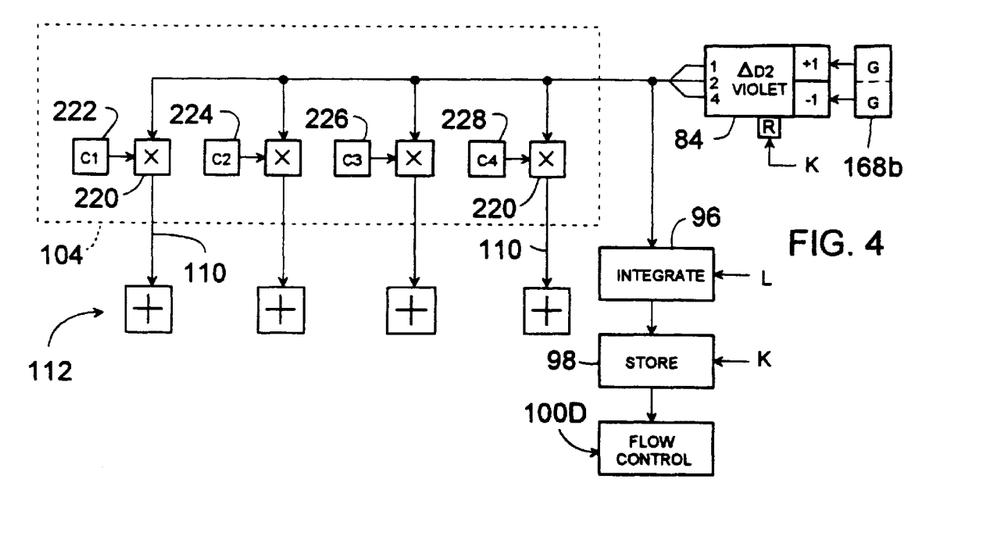
FIG. 4 is a schematic view showing a simplified spectral dye response simulator circuit.

Referring now to FIG. 4, there is shown the details of violet dye response simulator circuit 104 which includes four multiplying circuits 220 to each of which is applied the output of violet dye counter 84. Multiplying circuits 220 are provided with a further input from respective sources 222, 224, 226 and 228 which provide the respective coefficients C1, C2, C3 and C4.

Figure 11:
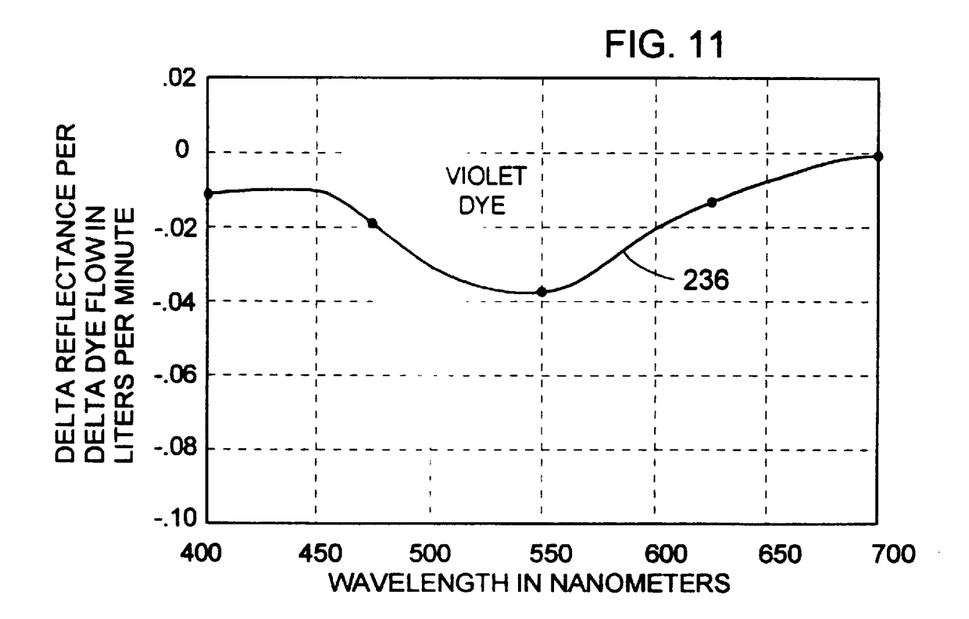
FIG. 11 is a graph of change in reflectance per change in dye flow for a violet dye at five end points of four bands in the visible spectrum.

Referring now to FIGS. 4 and 11, it will be seen that the coefficient C1 for the band from 400 to 475 nm has a mean value of approximately -0.013; the coefficient C2 for the band from 475 to 550 nm has a mean value of approximately -0.033; the coefficient C3 for the band from 550 to 625 nm has a mean value of approximately -0.024; and the coefficient C4 for the band from 625 to 700 nm has a mean value of approximately -0.005.

As shown in FIGS. 10 and 11, the spectral response curves for the blue and violet dyes have an ordinate representing change in reflectance divided by change in dye flow where the dye flow is measured in liters per minute. These curves are obtained by making a unit change in dye flow and measuring the resultant changes in reflectance for the various bands in the visible spectrum. It would be thought preferable that these response curves be measured when the dye flows are close to their correct values. However, it appears that the response curves remain substantially the same even if the dye flows vary widely from those which provide minimum errors from the desired target spectrum.

It will of course be understood that the spectral response curves of FIGS. 10 and 11 would have to be scaled if the speed or thickness of web 14 varies or if there is a change in fiber flow or concentration of a dye solution. Variation in web speed, web thickness, fiber flow and dye concentration may be compensated for by providing a multiplying circuit between each dye counter and dye response simulator circuit and making the factor of multiplication greater than unity or less than unity.

The additive response circuit 108 of FIG. 2 is constructed in the manner shown in FIG. 4; and for an additive spectral response curve similar to that of FIGS. 10 and 11, the ordinate would be change in reflectance divided by change in additive flow in liters per minute. Again, a multiplying circuit may be provided between additive counter 80 and additive response simulator circuit 108 so that changes in web speed, web thickness and additive concentration may be compensated for.

Figure 5:
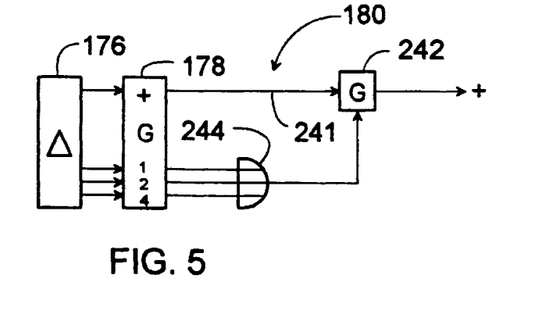
FIG. 5 is a schematic view showing a polarity discriminator circuit.

Referring now to FIG. 5, there are shown details of polarity discriminator 180. The sign output of comparator 176 is typically ON for both zero and positive outputs and OFF only for negative outputs. The sign output 241 of gate 178 is coupled through gate 242 to the "+" output of discriminator 180. The 1, 2, and 4 binary comparator outputs from gate 178 are applied to an OR circuit 244, the output of which enables gate 242. Thus gate 242 supplies a "+" discriminator output only if the binary comparator output from gate 178 is +1 or greater and not if the binary comparator output from gate 178 is zero or negative.

Figure 6:
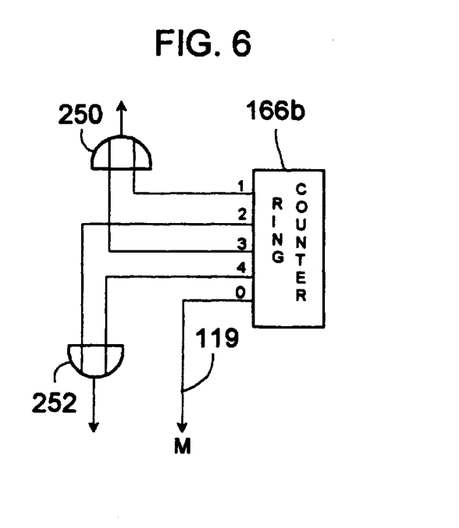
FIG. 6 is a schematic view showing a five-stage ring counter for providing iterative changes in dye flows during one correction cycle.

Referring now to FIG. 6, there is shown a five-stage ring counter 166b which replaces sequencing counter 166a of FIG. 3. The "1" output of counter 166b is coupled through OR circuit 250 to enable gates 168a; the "2" output of the counter is coupled through OR circuit 252 to enable gates 168b; the "3" output of the counter is coupled through OR circuit 250 to enable gates 168a; the "4" output of the counter is coupled through OR circuit 252 to enable gates 168b; and the "0" output of counter 166b again provides the M signal 119. This enables iterative corrections of first the blue dye counter 86, then the violet dye counter 84, then the blue dye counter 86, and finally the violet dye counter 84. Since the time for the correction cycle is doubled, this will require 64 timing pulses from source 152; and circuit 214 may now divide by 14,999,936.

Figure 7:
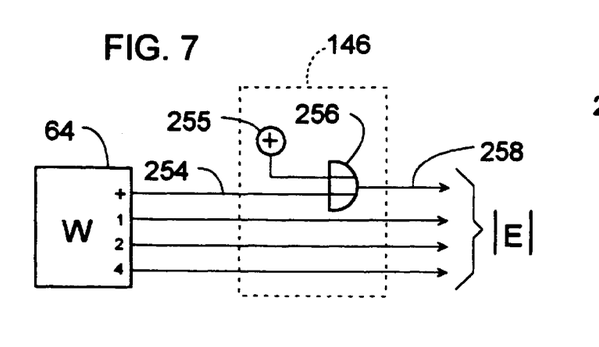
FIG. 7 is a schematic view showing a circuit for obtaining the absolute value of an error signal.

Referring to FIG. 7, there are shown the details of the absolute value circuit 146 of FIG. 3. The sign output 254 of the fourth weighting circuit 64 is coupled to one input of an OR circuit 256. A source of positive potential 255 is applied to the other input of OR circuit 256. The output of OR circuit 256 will thus be positive irrespective of the sign output 254 of the fourth weighting circuit 64.

Figure 8:
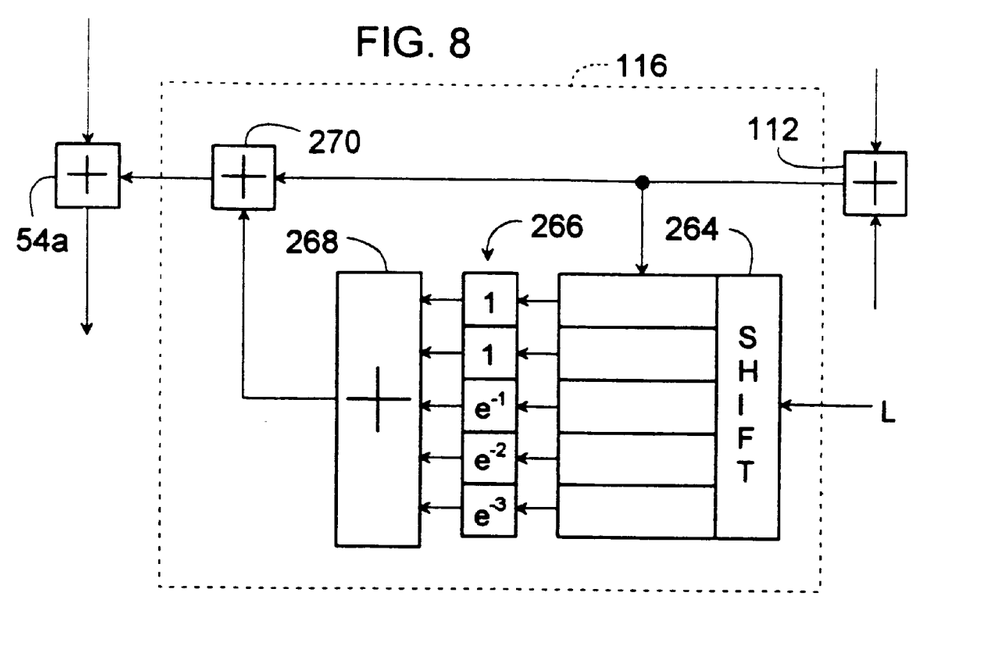
FIG. 8 is a schematic view showing a predictor circuit which compensates for the effects of time-constant and time delay.

Referring now to FIG. 8, there is shown the details of one of the prediction circuits 116. The output of summing circuit 112 is applied to a shift register 264 having, for example, five stages. The five stages are coupled to corresponding circuits indicated generally by 266 which multiply the signals of the various stages by 1, 1, $e^{-1}$, $e^{-2}$, and $e^{-3}$ respectively. The outputs of multiplying circuits 266 are applied to a summing circuit 268. The outputs of summing circuits 112 and 268 are combined in summing circuit 270; and the output of circuit 270 is applied to summing circuit 54a of FIG. 3 (or summing circuit 54 of FIG. 2). Register 264 is shifted by the L signal 118.

Figure 9:
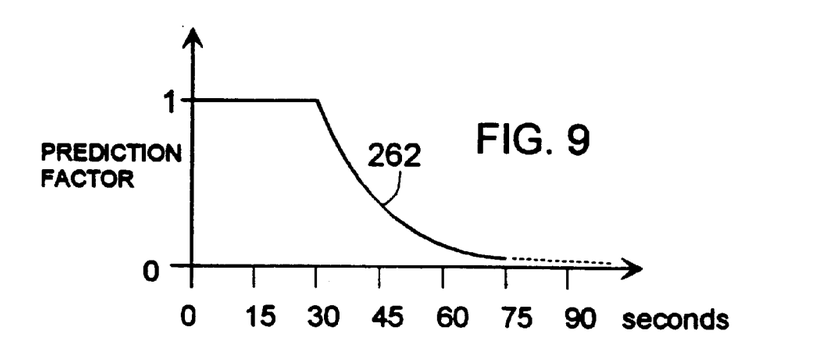
FIG. 9 is a graph illustrating the variation in the prediction factor with time.

When the outputs from the dye response circuits 104 and 106 have been optimized for a first time, corresponding to time zero of FIG. 9, the output of summing circuit 268 will be zero; and the outputs of summing circuits 112 and 270 will be identical. The prediction factor at time zero is therefore unity. For a time delay or transport lag of 30 seconds, the prediction factor is unity at 15 seconds and 30 seconds. Because of the 15 seconds time-constant of exponential change in dye flow at the output of headbox 18 to change in dye flow in pipe 21, the prediction factor drops to $e^{-1}$ at 45 seconds, $e^{-2}$ at 60 seconds, and $e^{-3}$ at 75 seconds. It will be understood that a further stage of shift register 264 and a further multiplier 266 may be provided, for example, to produce an $e^{-4}$ prediction factor at 90 seconds. The spectrophotometer 50 measures no change in reflectance of web 14 due to a change in dye flow in pipe 21 until 30 seconds have elapsed from such change in dye flow. Thereafter spectrophotometer 50 measures an exponentially increasing portion of such change during the period from 30 to 75 seconds, for example. Ideally for each wavelength band the summation of the output of prediction circuit 116 and the changes in output of spectrophotometer 50 should be a constant equal to the output of summing circuit 112 for the first correction cycle, so that no further corrections need be made during subsequent correction cycles. Prediction circuit 116 is commonly referred to as a Smith predictor. If the period between correction cycles is halved to 7.5 seconds, then the number of stages of shift register 264 and the number of multiplying circuits 266 may each be doubled. The respective prediction factors would be 1, 1, 1, 1, $e^{-0.5}$, $e^{-1}$, $e^{-1.5}$, $e^{-2}$, $e^{-2.5}$, and $e^{-3}$.

It will be understood that where the time-constant of exponential response is substantially zero and there is no time delay or transport lag between application of dyes to an article and measurement of the spectrum produced by such changes in application of dyes, then prediction circuits 116 are much simplified; and the application of dyes to an article can be controlled substantially continuously.

In such a simplified or degenerate prediction circuit 116, components 264, 266, 268 and 270 may be omitted; and the output of summing circuit 112 is directly applied to adding circuit 54a or 54.

Where surface coatings such as pigmentation and sizing are to be applied to web 14 by press rollers 23 of FIG. 1, it is preferable to control the thickness of the films on rollers 23 by doctor blades or rods (not shown), the spacing of which from the surfaces of roller 23 is adjustable. Changes in thickness of the surface coating films are treated in a manner similar to changes in flow of dye or additive to pipe 21. The normalized response curve ordinate would be the change in reflectance divided by the change in doctor blade spacing. For surface coatings applied by press rolls 23 the time-constant of system response is substantially zero. Since the press rolls 23 are disposed upstream of spectrophotometer 50, there is a transport lag or time delay; but if the period between correction cycles is greater than this time delay, then the simplified or degenerate prediction circuit 116 previously described may be used.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. For example, the wavelength bands need not be of equal widths. Instead of weighting the inputs to the non-linear operations circuits 68, the outputs thereof may be weighted before application to summing circuit 72. Instead of employing various circuits and devices operating simultaneously in parallel, the effects provided may be obtained serially by time-sharing as by appropriate programming of a general purpose computer. Thus for the dye simulator circuit of FIG. 4, a single multiplier 220 could receive the four coefficients as sequential inputs. It is therefore to be understood that my invention is not to be limited to the specific details shown and described.

Having thus described my invention, what I claim is:

1. A method of controlling the color of an article including the steps of applying a first number of colorants to the article, measuring the reflectances of the article in a second number of wavelength bands spanning the visible spectrum which is greater than the first number and at least four, providing desired reflectances of the article in the same wavelength bands spanning the visible spectrum, providing for each colorant in each of the same wavelength bands spanning the visible spectrum the expected change in reflectance which would result from a change in the application of the colorant to the article, algebraically combining the measured reflectances and the desired reflectances and the expected changes in reflectances to provide a number of error signals equal to the second number, performing a non-linear operation on each of said error signals to provide corresponding modified signals, summing the modified signals, and adjusting the amount of each colorant applied to the article such that the result of the summing step is a minimum.

2. Apparatus for controlling the color of an article including in combination means for applying a first number of colorants to the article, means for measuring the reflectances of the article in a second number of wavelength bands spanning the visible spectrum which is greater than the first number and at least four, means for providing desired reflectances of the article in the same wavelength bands spanning the visible spectrum, simulating means for providing for each colorant in each of said wavelength bands the expected change in reflectance which would result from a change in the application of the colorant to the article, means linearly responsive to the measured reflectances and the desired reflectances and the expected changes in reflectances provided by the simulating means for providing a number of error signals equal to the second number, means for summing providing an output, means including means for performing a non-linear operation for coupling the error signals to the summing means, and means responsive to the summing means for adjusting the amount of each colorant applied to the article such that the output of the summing means is a minimum.

3. Apparatus as in claim 2 wherein the non-linear operation means comprises means for raising a numerical representation to an even power.

4. Apparatus as in claim 3 wherein the power is two.

5. Apparatus as in claim 2 wherein the non-linear operation means comprises means for obtaining the absolute value of a numerical representation.

6. Apparatus as in claim 5 further including means for raising said absolute value to a power ranging from less than unity to more than two.

7. Apparatus as in claim 2 wherein the means providing the error signals comprises means for algebraically combining the measured and desired reflectances and the expected changes in reflectances provided by the simulating means.

8. Apparatus as in claim 2 wherein the simulating means includes means providing a numerical representation of a change in the application of the colorant to the article, means for providing in each of the wavelength bands a response signal representing the actual change in reflectance resulting from a predetermined change in the application of the colorant to the article, and means for multiplying said numerical representation by each of the response signals.

9. Apparatus as in claim 8 wherein the colorant adjusting means includes means for initially adjusting said numerical representation such that the output of the summing means is a minimum and means responsive to the adjusted representation for subsequently producing a corresponding change in the application of the colorant to the article.

10. Apparatus as in claim 2 wherein the means coupling one of the error signals to the summing means includes means for weighting.

11. Apparatus as in claim 10 wherein one error signal is applied to the weighting means which provides an output and wherein the output of the weighting means is applied to the non-linear operation means.

12. Apparatus as in claim 2 further including means responsive to the measured reflectances for providing three measured color coordinates in a predetermined color space, means for providing three desired color coordinates in the same color space, means responsive to the measured color coordinates and the desired color coordinates for providing three further error signals, and means including the non-linear operation means for coupling the three further error signals to the summing means.

13. Apparatus as in claim 12 wherein the means coupling one of the further error signals to the summing means includes means for weighting.

14. Apparatus as in claim 13 wherein said one further error signal is applied to said weighting means which provides an output and wherein the output of the weighting means is applied to the non-linear operation means.

15. Apparatus as in claim 2 further including means providing a colorant signal proportional to the amount of a colorant applied to the article and means coupling the colorant signal to the summing means.

16. Apparatus as in claim 15 wherein the colorant signal coupling means includes means for weighting.

17. Apparatus as in claim 15 wherein the colorant signal coupling means includes means for raising a numerical representation to a power ranging from less than unity to more than two.

18. Apparatus as in claim 2 further including means providing a number of predictions equal to the second number, the prediction means providing outputs which compensate for time delay between application of a colorant to the article and measurement of reflectances resulting therefrom, wherein the means providing the error signals comprise means for algebraically combining the measured and desired reflectances and the outputs of the prediction means.

19. Apparatus as in claim 2 wherein the article is a web of paper and the colorant is a dye, further including a headbox having an inlet provided with a slurry of pulp and water, and having an outlet at which the paper web is formed, the applying means comprising means for injecting the dye into the inlet slurry, means providing a number of predictions equal to the second number, the prediction means providing outputs which compensate for the time-constant of exponential change in amounts of dye at the outlet of the headbox resulting from a change in amount of dye injected, wherein the means for providing the error signals comprise means for algebraically combining the measured and desired reflectances and the outputs of the prediction means.

20. Apparatus as in claim 19 further including means for injecting an additive into the inlet slurry, said additive affecting the measured reflectances, and means for providing in each of said wavelength bands the expected change in reflectances which would result from a change in the amount of additive injected.

21. Apparatus for controlling the color of an article including in combination means for applying a colorant to the article, means for measuring the reflectance of the article in a number of at least four wavelength bands spanning the visible spectrum, means including means responsive to the measuring means for providing three measured color coordinates in a given color space, means for providing three corresponding desired color coordinates in the same color space, means for comparing, means coupling a measured color coordinate and the corresponding desired color coordinate to the comparing means, means responsive to the comparing means for providing an error signal, and means responsive to the error signal for adjusting the amount of colorant applied to the article, the adjusting means including simulating means for providing in each of said wavelength bands the expected change in reflectance which would result from a change in the application of the colorant to the article, and the means responsive to the measuring means comprising means for algebraically combining the measured reflectances and the expected changes in reflectances provided by the simulating means.

22. A method of controlling the color of an article including the steps of applying a colorant to the article, measuring the reflectance of the article in a number of at least four wavelength bands spanning the visible spectrum, utilizing the measured reflectances to provide three measured color coordinates in a given color space, providing three corresponding desired color coordinates in the same color space, comparing a measured color coordinate and the corresponding desired color coordinate to provide an error signal, utilizing the error signal to adjust the amount of colorant applied to the article and to provide in each of said wavelength bands the expected change in reflectance which would result from a change in the application of the colorant to the article, and algebraically combining said expected changes in reflectances and said measured reflections in the step providing the three measured color coordinates.

* * * * *

UNITED STATES PATENT AND TRADEMARK OFFICE
CERTIFICATE OF CORRECTION

PATENT NO. : 6,052,194
DATED : April 18, 2000
INVENTOR(S) : Seyan Nuyan

It is certified that error appears in the above-identified patent and that said Letters Patent is hereby corrected as shown below:

On the title page,
"item [56]" References Cited" there should be added --4,439,038 3/1984 Mactaggart... 356/408- -

Signed and Sealed this

Twenty-seventh Day of February, 2001

Attest:

NICHOLAS P. GODICI

Attesting Officer        Acting Director of the United States Patent and Trademark Office